US008823396B2

(12) United States Patent
Astley et al.

(10) Patent No.: US 8,823,396 B2
(45) Date of Patent: Sep. 2, 2014

(54) APPARATUS AND ASSOCIATED METHODS

(71) Applicant: Nokia Corporation, Espoo (FI)

(72) Inventors: Michael Robert Astley, Waterbeach (GB); Stefano Marco Borini, Cambridge (GB); Jani Kivioja, Cambridgeshire (GB); Teuvo Tapani Ryhanen, Helsinki (FI); Elisabetta Spigone, Cambridge (GB); Di Wei, Cambridge (GB); Richard White, Huntingdon (GB)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 13/739,452

(22) Filed: Jan. 11, 2013

(65) Prior Publication Data

US 2014/0197851 A1    Jul. 17, 2014

(51) Int. Cl.
*G01R 27/26*    (2006.01)
(52) U.S. Cl.
USPC ........... 324/660; 324/661; 324/663; 324/664; 324/665; 324/679
(58) Field of Classification Search
CPC .............. G01R 27/26; G01R 27/2641; G01R 27/2605; G01R 17/00; G01D 5/241; G01D 5/2412; G01D 5/2417
USPC ........ 324/659–690, 694; 73/335.01, 780, 304
See application file for complete search history.

(56) References Cited

U.S. PATENT DOCUMENTS

| | | | | |
|---|---|---|---|---|
| 4,743,836 A | * | 5/1988 | Grzybowski et al. | 324/678 |
| 5,581,193 A | * | 12/1996 | Weiss et al. | 324/76.19 |
| 6,704,679 B1 | | 3/2004 | Coni et al. | 702/127 |
| 6,744,258 B2 | * | 6/2004 | Ishio et al. | 324/548 |
| 2005/0012028 A1 | | 1/2005 | Weaver et al. | 250/208.2 |
| 2007/0262963 A1 | | 11/2007 | Xiao-Ping et al. | 345/173 |
| 2010/0123658 A1 | | 5/2010 | Demuynck et al. | 345/157 |

(Continued)

FOREIGN PATENT DOCUMENTS

| | | |
|---|---|---|
| JP | 3188669 B2 | 7/2001 |
| WO | WO 2005/008196 A2 | 1/2005 |
| WO | WO 2012/054350 A1 | 4/2012 |

OTHER PUBLICATIONS

Wang, S., et al., "High Mobility, Printable, and Solution-Processed Graphene Electronics", NANO Letters, © 2010 American Chemical Society, 7 pgs.

(Continued)

*Primary Examiner* — Patrick Assouad
*Assistant Examiner* — Alexander J Nemtzow
(74) *Attorney, Agent, or Firm* — Harrington & Smith

(57) ABSTRACT

An apparatus including a sensor array, configured to produce an array output value in response to an environmental stimulus, and a controller, the sensor array including a plurality of sensors and a common output terminal connected to the respective outputs of the sensors, each sensor having first and second electrodes configured to output a respective sensor output value in a particular environment based on the areas of the first and second electrodes and/or the spacing therebetween, the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value.

20 Claims, 11 Drawing Sheets

(56) References Cited

U.S. PATENT DOCUMENTS

| | | | |
|---|---|---|---|
| 2010/0327882 A1 | 12/2010 | Shahparnia et al. | 324/659 |
| 2011/0193791 A1 | 8/2011 | Tong et al. | 345/173 |
| 2012/0043970 A1 | 2/2012 | Olson | 324/601 |
| 2012/0206154 A1 | 8/2012 | Pant et al. | 324/613 |

OTHER PUBLICATIONS

Janata, J. et al., "conducting polymers in electronic chemical sensors". © 2002 Nature Publishing Group, 6 pgs.

Pantazis, N.A., et al., "Capacitive sensor arrays for the real time detection of volatile organic compounds", © 2011 IEEE, 4 pgs.

Seacoast Science, Inc., Chemical Sensor Company, production Information, www.seacoastscience.com, Nov. 19, 2012, 2 pgs.

Courbat, J., et al., "Inkjet Printing on Paper for the Realization of Humidity and Temperature Sensors", © 2011 IEEE, 4 pgs.

Igreja, R, et al., "Analytical evaluation of the interdigital electrodes capacitance for a multi-layered structure", © 2004 Elsevier B.V., 11 pgs.

Villares, G., et al., A Non-linear Model of Sensitivity Matrix for Electrical Capacitance Tomography:, Proceedings of the 2012 Electrostatics Joint Conference, Cambridge, Ontario, Canada, Jun. 12-14, 2010, 4 pgs.

Li, B., et al., "Inkjet printed chemical sensor array based on polythiophene conductive polymers", © 2006 Elsevier B.B., 10 pgs.

Pritchard, E., et al., "Flexible Capacitive Sensors for High Resolution Pressure Measurement", © 2008 IEEE, 4 pgs.

Zhao, C-L., et al., "Humidity Sensing Properties of the Sensor Based on Graphene Oxide Films with Different Dispersion Concentrations", © 2011 IEEE, 4 pgs.

Fraden, J., "Handbook of Modern Sensors, Physics, Designs, and Applications", © Springer Science, Business Media, LLC 2010, pp. 62-67 and pp. 208-211.

\* cited by examiner

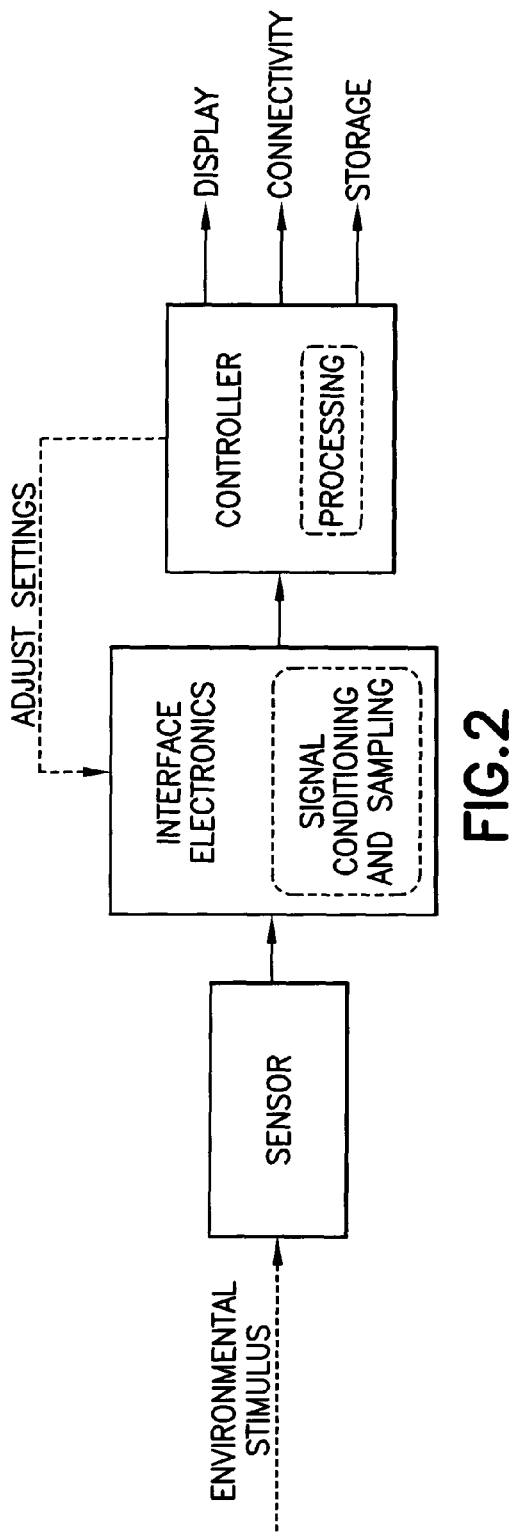
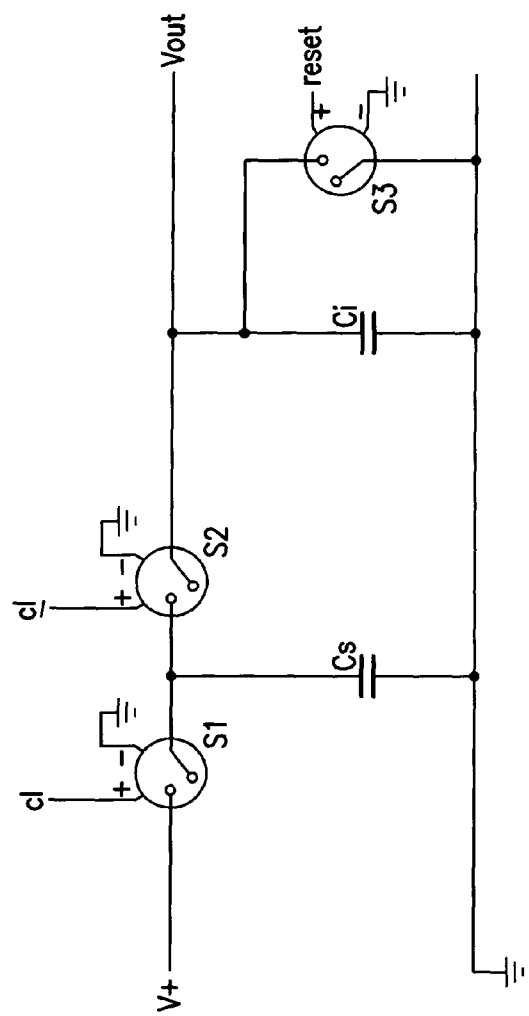

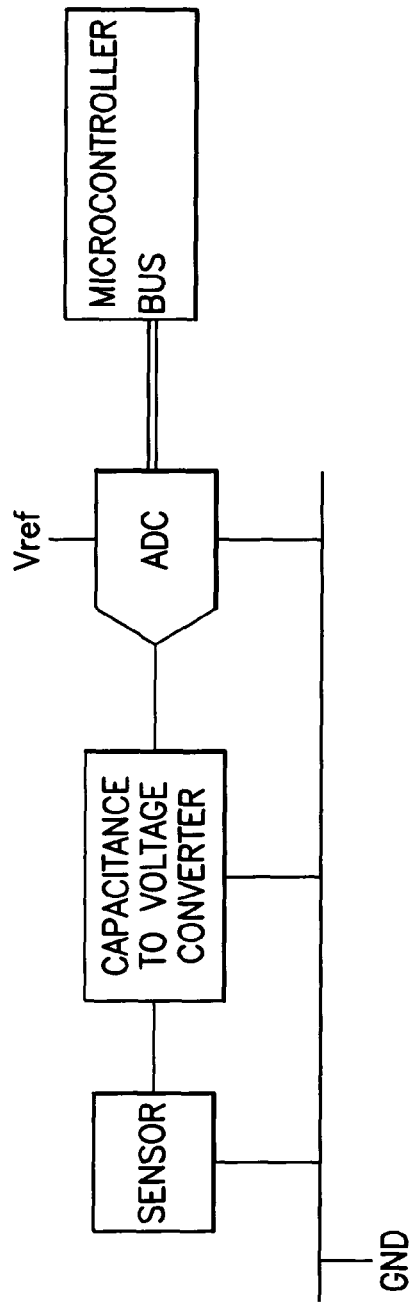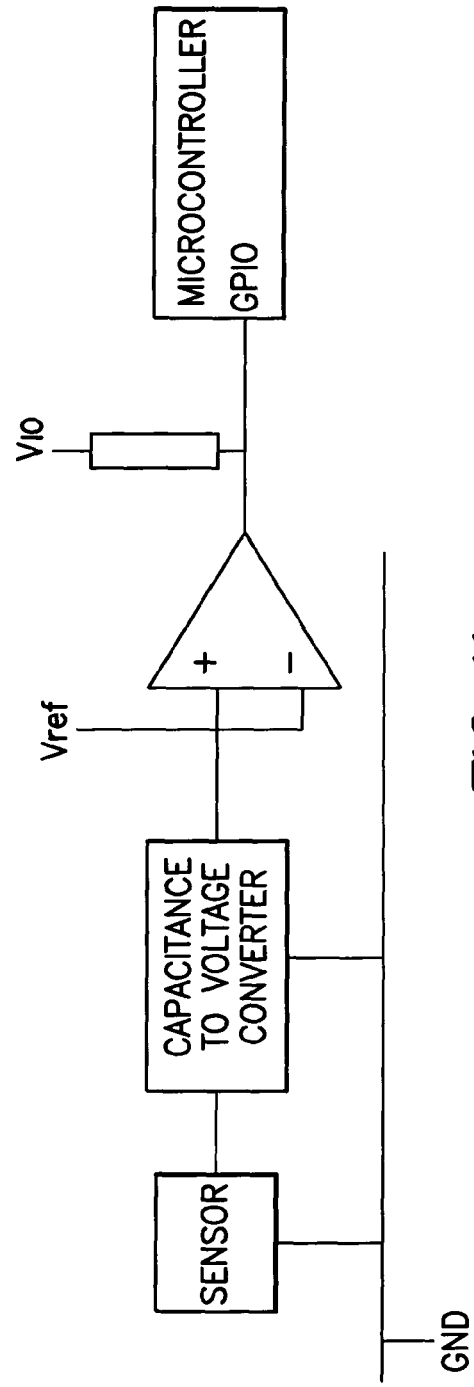

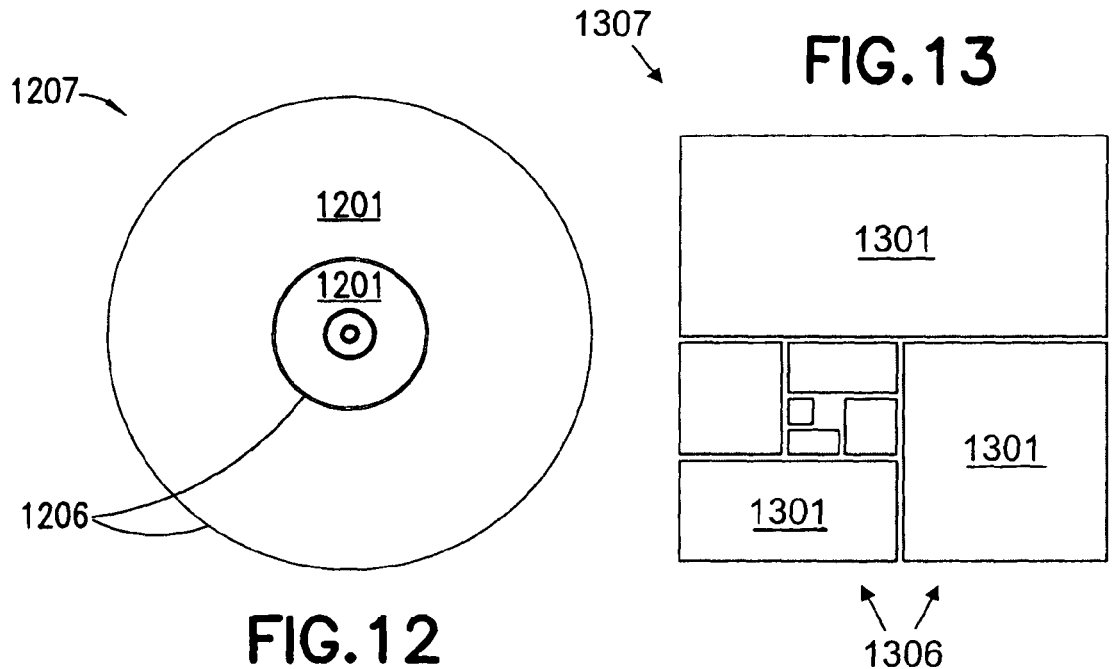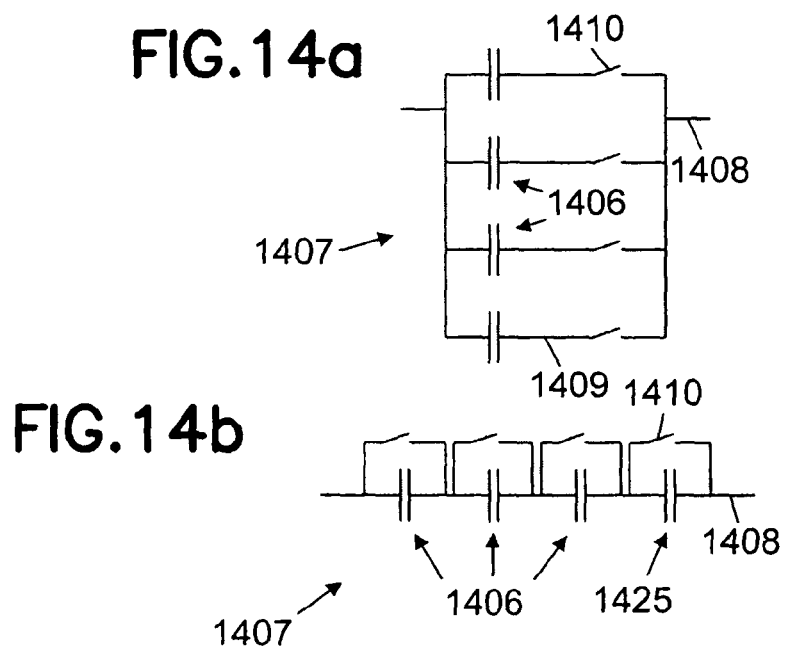

APPARATUS AND ASSOCIATED METHODS

TECHNICAL FIELD

The present disclosure relates to the field of environmental sensors, associated methods and apparatus, and in particular concerns a sensor array which enables the complexity of the measurement electronics to be reduced. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

There is currently a demand for low-cost environmental sensors which produce an electrical output signal that is dependent upon one or more physical parameters (such as temperature and/or humidity). With many materials, however, the non-linear sensitivity of the electrical properties to certain parameters means that analogue signal conditioning is required. Analogue electronics are typically costly and power hungry compared with digital electronics because of the need to keep noise to a minimum. The requirement for analogue measurement electronics therefore increases the cost and complexity of the sensors considerably.

The apparatus and methods disclosed herein may or may not address this issue.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an apparatus comprising a sensor array, configured to produce an array output value in response to an environmental stimulus, and a controller, the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween, the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value.

The reference value may be a substantially constant threshold value. The controller may be configured to control the switches to hold the array output value at the threshold value. The apparatus may be configured to enable measurement of the environmental stimulus using the configuration of the switches when the array output value is at the threshold value. The apparatus may be configured to allow a plurality of different switch configurations. Each configuration may correspond to a different environmental stimulus value. The apparatus may be configured to enable measurement of the environmental stimulus using a predetermined calibration of the different switch configurations.

The reference value may be a predefined range. The controller may be configured to control the switches to hold the array output value within the predefined range. The apparatus may be configured to enable measurement of the environmental stimulus using the array output value when the array output value is within the predefined range. The apparatus may be configured to allow a plurality of different switch configurations. Each configuration may correspond to a different range of environmental stimulus values. The apparatus may be configured to enable measurement of the environmental stimulus using a predetermined calibration of the current switch configuration in combination with the array output value.

The apparatus may be configured such that the area of the first and/or second electrode of the respective sensors increases between adjacent sensors of the sensor array. The area of the first and/or second electrode may increase exponentially, double or increase by an order of magnitude from one sensor of the sensor array to the adjacent sensor.

The apparatus may be configured such that the spacing between the first and second electrodes of the respective sensors increases between adjacent sensors of the sensor array. The spacing between the first and second electrodes may increase exponentially, double or increase by an order of magnitude from one sensor of the sensor array to the adjacent sensor.

The sensors, or their respective first electrodes, may have a regular spacing in one, two or three dimensions between one another. The sensors, or their respective first electrodes, may form a concentric or semi-concentric sensor/electrode array. The sensors, or their respective first electrodes, may be arranged to form a series of adjacent sensors/electrodes which spiral outward from the centre of the sensor array.

The first and/or second electrodes of the respective sensors may be arranged to form an array of interdigitated or parallel plate electrodes. The sensors may be connected to one another in series or in parallel. The sensors may be capacitive, resistive, inductive, current or voltage source (e.g. photodiodes) sensors. Each sensor may comprise a dielectric material configured to prevent a flow of electrical current between the first and second electrodes in order to produce the respective output.

The switches may be analogue switches or field-effect transistors.

The environmental stimulus may be one or more of the concentration of a chemical or biological species in the environment in which the sensor array is located, the concentration of a liquid or gas in said environment, the relative humidity of said environment, the temperature of said environment, and the pressure applied to one or more sensors of the sensor array. Each sensor may exhibit one or more of a non-linear and an exponential response to the environmental stimulus.

The apparatus may be one or more of an electronic device, a portable electronic device, a portable telecommunications device, a sensor, and a module for one or more of the same.

The apparatus may comprise an interface circuit connected between the sensor array and the controller. The interface circuit may be configured to convert the array output value into a form which is suitable for use by the controller. The interface circuit may comprise one or more of a capacitance-to-voltage converter, a relaxation oscillator, and a switched capacitor sigma-delta arrangement. The apparatus may comprise a measurement circuit configured to measure the array output value. The measurement circuit may comprise an analogue-to-digital converter or a comparator.

According to a further aspect, there is provided a method involving the use of an apparatus, the apparatus comprising a sensor array, configured to produce an array output value in response to an environmental stimulus, and a controller, the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween, the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value, wherein the method comprises controlling, by the controller, which of the sensors are connected to the common output terminal using the respective switches to vary the effective area and/or spacing of the sensor array such that the array output value at the common output terminal, based on the contribution of the respective sensor output values of the connected sensors, is held at a reference value.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

According to a further aspect, there is provided a computer program comprising computer code configured to control the use of an apparatus, the apparatus comprising a sensor array, configured to produce an array output value in response to an environmental stimulus, and a controller, the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween, the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value, wherein the computer code is configured to control, with the controller, which of the sensors are connected to the common output terminal using the respective switches to vary the effective area and/or spacing of the sensor array such that the array output value at the common output terminal, based on the contribution of the respective sensor output values of the connected sensors, is held at a reference value.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

FIG. 2 shows a typical sensing system;

FIG. 3a shows a capacitance-to-voltage converter;

FIG. 4a shows a sensing system comprising an analogue-to-digital converter for measuring the output value of the sensor;

FIG. 4b shows a sensing system comprising a comparator circuit for measuring the output value of the sensor;

FIG. 12 shows a sensor array having a concentric electrode arrangement;

FIG. 13 shows a sensor array having a spiraling electrode arrangement;

FIG. 14a shows a sensor array in which the individual sensors are connected to one another in parallel;

FIG. 14b shows a sensor array in which the individual sensors are connected to one another in series;

FIGS. 7-17, in particular, relate to particular embodiments of the present disclosure.

DESCRIPTION OF SPECIFIC ASPECTS/EMBODIMENTS

Figure 1A:
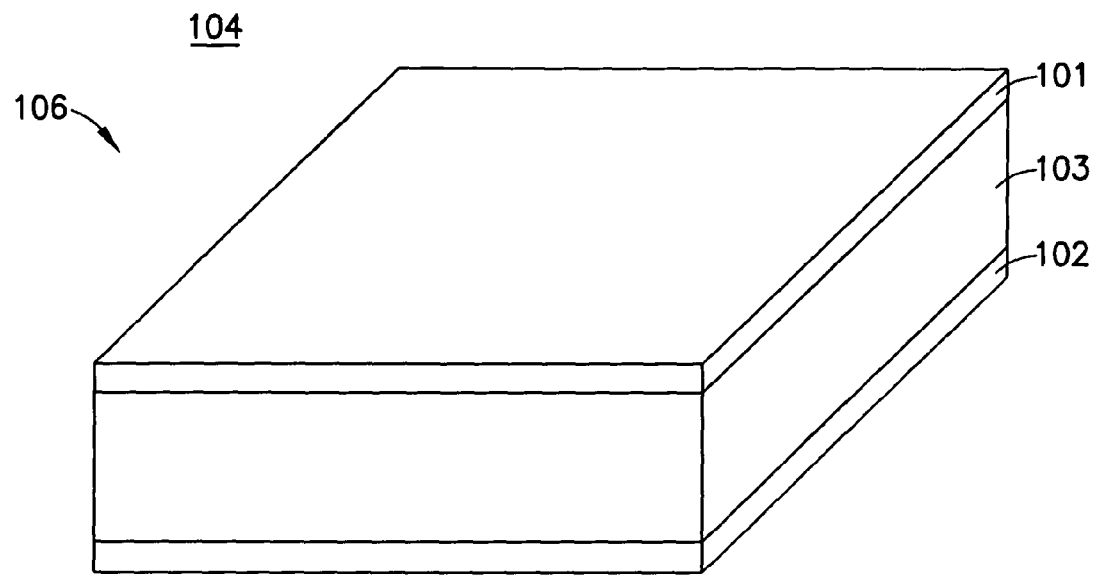
FIG. 1a shows a parallel plate capacitive sensor.

A capacitive sensor 106 comprises first 101 and second 102 electrodes separated by a dielectric material 103. The electrodes typically have a parallel plate (FIG. 1a) or interdigitated (FIG. 1b) configuration. In the parallel plate configuration, one or both of the electrodes 101, 102 may be porous to allow the sensor 106 to interact with the surrounding environment 104. In the interdigitated configuration, the electrodes 101, 102 are usually supported on an underlying substrate 105 with the dielectric material 103 deposited on top of the electrodes 101, 102 and substrate 105.

The capacitance of a capacitive sensor is generally given by $$C = \epsilon_0 \epsilon_r G(A,d) \qquad \text{Equation 1}$$

where $\epsilon_0$ is the permittivity of free space, $\epsilon_r$ is the relative permittivity of the dielectric material 103, A is the area of the electrodes 101, 102, d is the spacing therebetween and G is a function that depends on the sensor geometry (which simplifies to A/d for parallel plate capacitive sensors). For some materials, such as poly(3-octylthiophene) or graphene oxide, $\epsilon_r$ is a function of an environmental parameter (e.g. humidity) meaning that the sensor's capacitance is directly related to this parameter.

In addition to the sensor itself, a sensing system (illustrated in FIG. 2) typically comprises a controller, which is responsible for controlling the sensor and can also be responsible for processing the sensor data, and interface electronics connected between the sensor and the controller configured to convert the sensor output into a form which is suitable for use by the controller. The controller may also be configured to send signalling to other device components to enable the storage, display and transmission of the sensor data. In addition, the controller may be configured to adjust the settings (e.g. gain or offsets) of the interface electronics in response to the received sensor data in order to avoid saturation of the signal.

A wide variety of interface electronics have been developed for capacitive sensing systems. Examples include capacitance-to-voltage converters, relaxation oscillators and switched capacitor sigma-delta arrangements. In a capacitance-to-voltage converter (shown in FIG. 3a), two switches ($S_1$ and $S_2$) are driven by out-of-phase voltage pulses to repeatedly charge and discharge the capacitive sensor ($C_s$). During each cycle when switch $S_1$ is closed, a quantity of charge ($Q \approx V_+ C_s$) flows onto the sensor from the positive supply (assuming that $V_+$ remains much greater than the voltage of an integration capacitor). When switch $S_1$ opens and switch $S_2$ closes, the charge flows from the sensor to the integration capacitor ($C_i$) increasing the voltage at the output by $Q/C_i$. After N cycles, therefore, the voltage at the output is given by $$V_{out} \approx N V_+ C_s / C_i \qquad \text{Equation 2}$$

which is proportional to the sensor capacitance. A reset switch ($S_3$) is used to clear the charge from the integration capacitor between measurements. Many sensor materials exhibit leakage due to an equivalent parallel resistance which allows charge stored on the sensor to dissipate. The switching period therefore must be substantially shorter than the RC constant of the sensor to prevent this leakage from distorting the results.

Figure 3B:
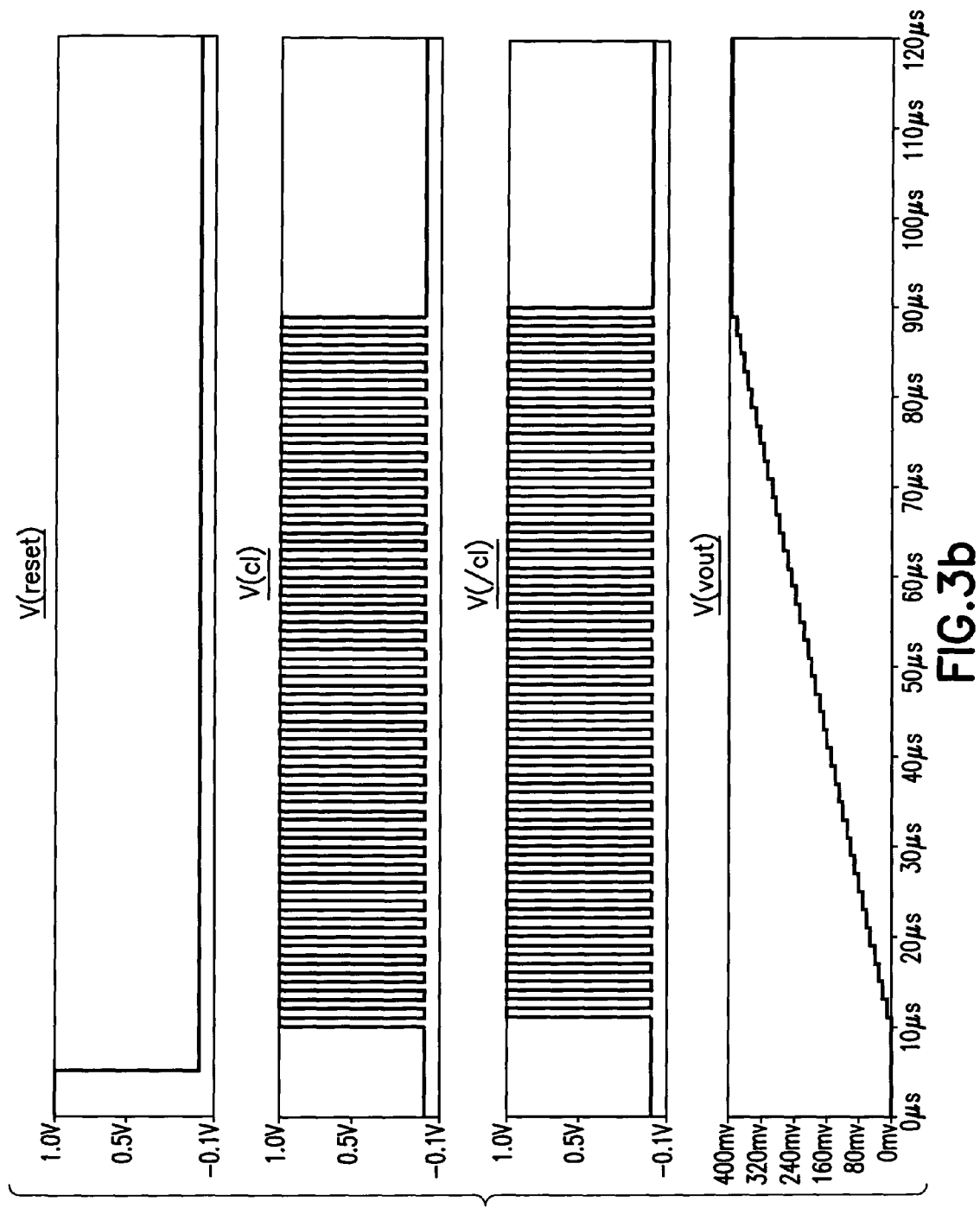
FIG. 3b shows how the output voltage of a capacitance-to-voltage converter varies with time.

FIG. 3b shows the voltage signals applied to switches $S_1$, $S_2$ and $S_3$ together with the resulting output voltage. The output voltage can then be sampled by an analogue-to-digital converter (as shown in FIG. 4a) to give an absolute capacitance reading, or a reference voltage and comparator (as shown in FIG. 4b) can be used to provide a threshold measurement which is triggered when the sensor has a predefined value of capacitance.

Figure 5:
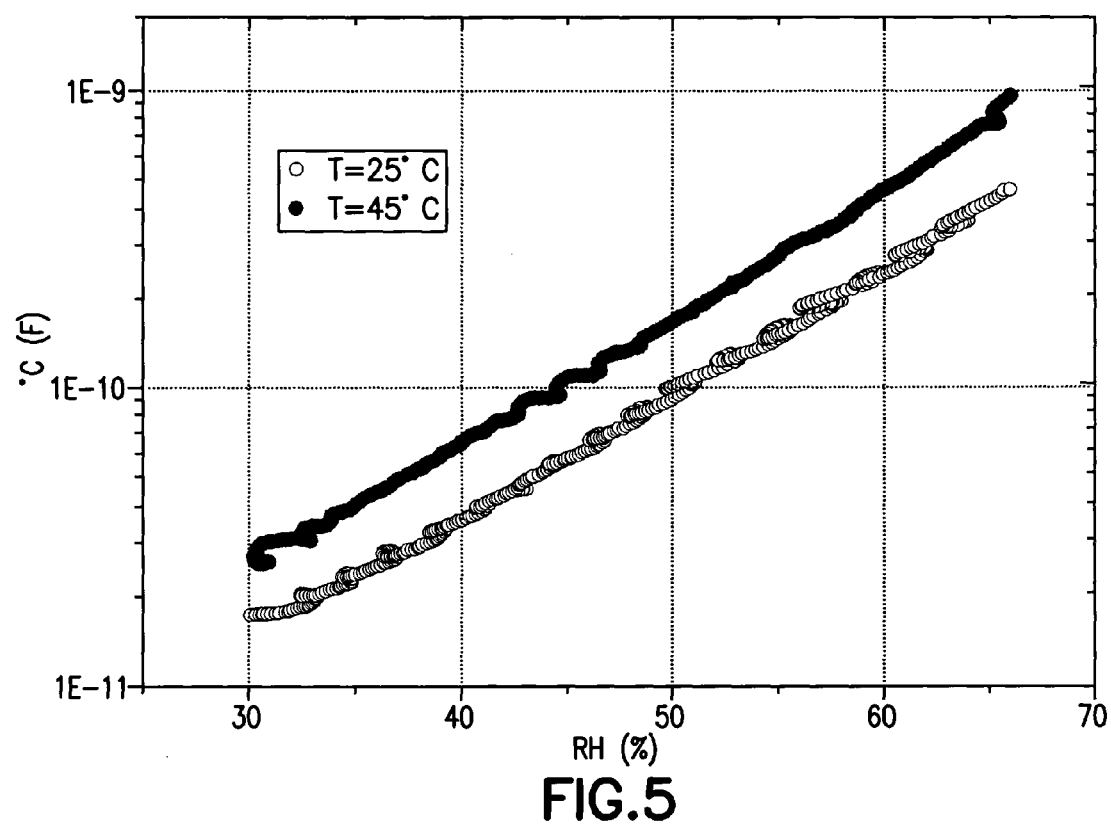
FIG. 5 shows the capacitance of graphene oxide as a function of relative humidity at two different temperatures.

As mentioned in the background section, some sensor materials exhibit a non-linear electrical response to certain environmental parameters. One example is the observed parallel capacitance of a graphene oxide film which varies exponentially (see logarithmic y-axis) with relative humidity (as shown in FIG. 5). This non-linear behaviour severely limits the input range over which the sensing system can provide an accurate measurement without the need for additional analogue components such as logarithmic or variable gain amplifiers.

The apparatus and methods disclosed herein may or may not address this issue. Whilst the following discussion refers to capacitive sensing systems, the present techniques are applicable to other sensing systems as well, e.g. resistive or inductive systems. In a resistive or inductive sensing system, each sensor of the array would be configured such that its resistance or inductance (respectively) varies with one or more environmental parameters (e.g. temperature and/or humidity). In this scenario, a change in the area and/or spacing of the first and second electrodes may be used to compensate for the variation in resistance or induction.

The present techniques can also be applied to sensors that act as current or voltage sources. For example, a photodiode operated in photoconductive mode behaves as a current source, whilst a photodiode operated in photovoltaic mode behaves as a voltage source. For current source sensors, the sensors must be connected in a parallel configuration. Then, because of Kirchoff's first law, the current of the combined sensors is the sum of the individual sensor currents (c.f. Equation 3, later). In this case, a transimpedance amplifier (current-to-voltage converter) is used in the interface electronics. For voltage source sensors, on the other hand, the sensors are arranged in a series configuration. Kirchoff's second law means that in this case, the output voltage is the sum of the individual voltages produced by each sensor (again, c.f. Equation 3).

Figure 6A:
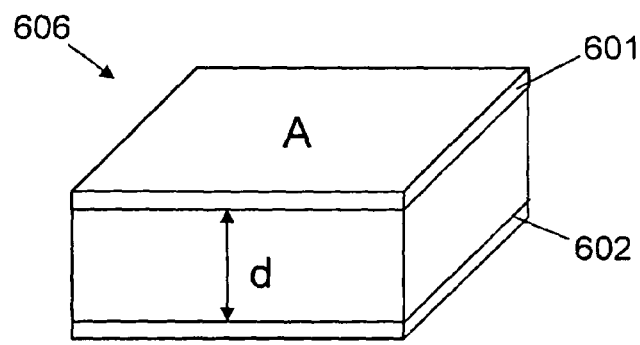
FIG. 6a shows the electrode area and spacing of a parallel plate capacitive sensor.
Figure 6B:
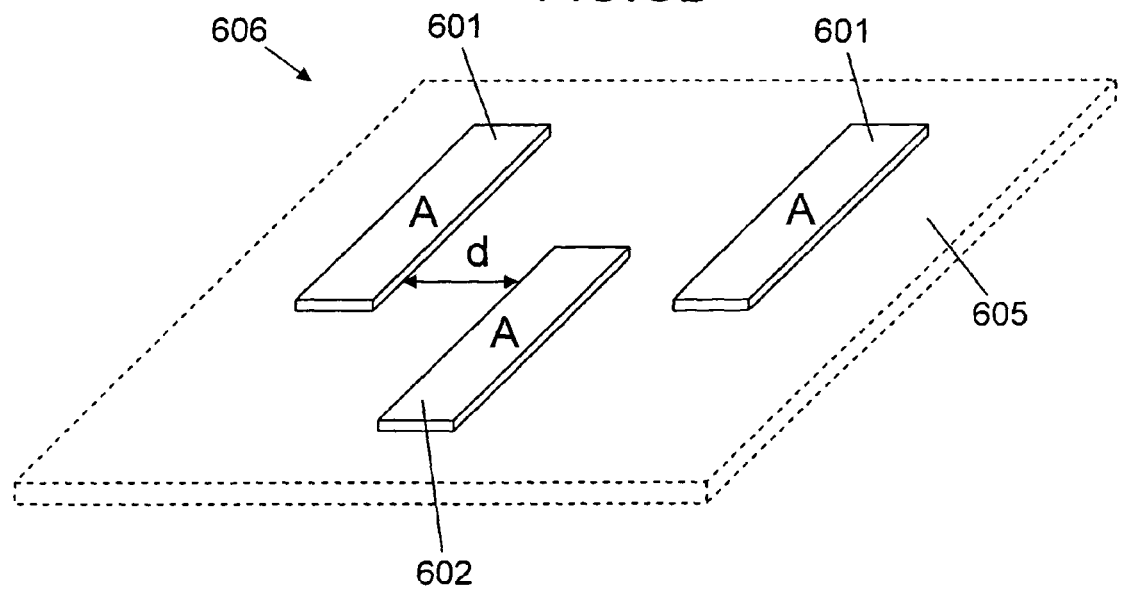
FIG. 6b shows the electrode area and spacing of an interdigitated capacitive sensor.

As shown by Equation 1, and illustrated in FIGS. 6a and 6b, the capacitance of a parallel plate (FIG. 6a) or interdigitated (FIG. 6b) capacitive sensor 606 depends on the area (A) and spacing (d) of the electrodes 601, 602. This aspect is exploited in the present apparatus to create an alternative method of measuring the environmental stimulus.

Figure 7:
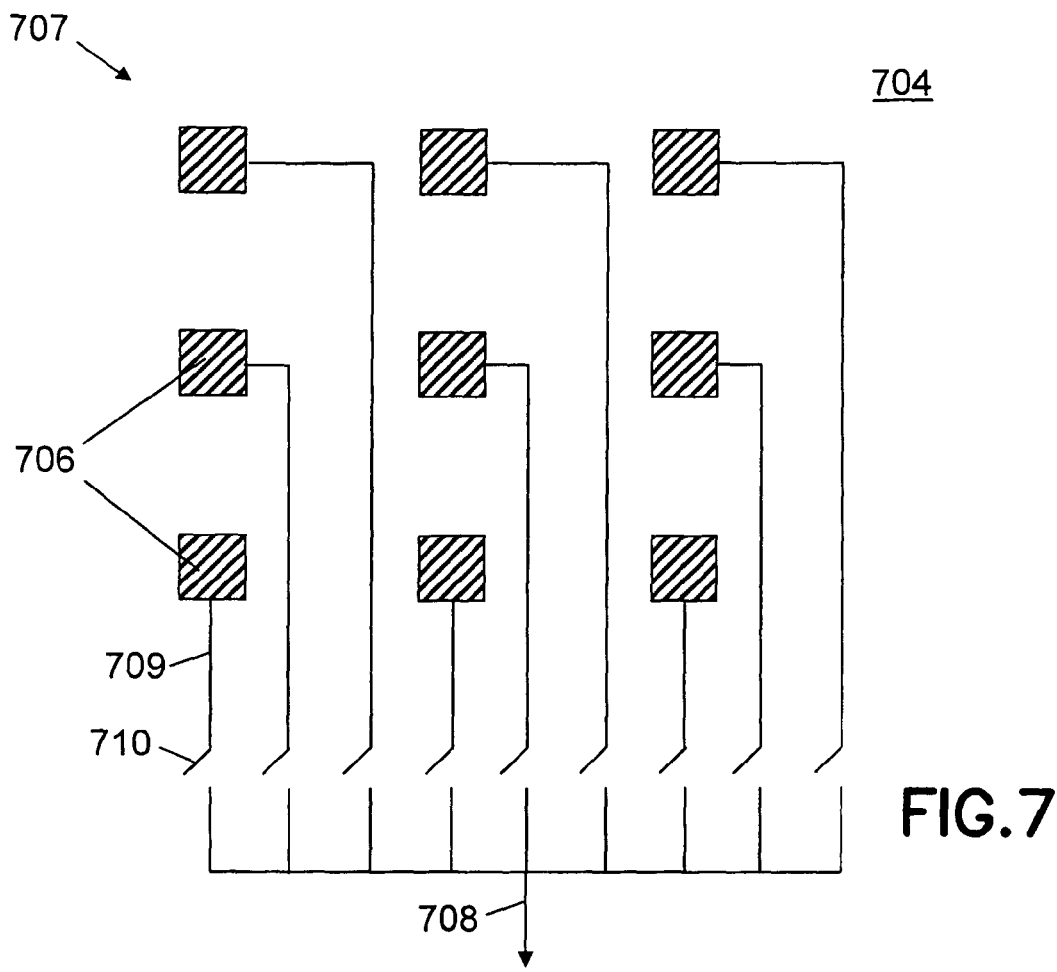
FIG. 7 shows a 3×3 sensor array comprising a plurality of identical sensors connected to a common output terminal by respective switches.

The present apparatus comprises a sensor array 707 (one example of which is shown in plan view in FIG. 7) configured to produce an array output value in response to an environmental stimulus. The sensor array comprises a plurality of sensors 706 (in this case a 3×3 array of sensors 706) and a common output terminal 708 connected to the respective outputs 709 of the sensors 706. Each sensor 706 has first and second electrodes configured to output a respective sensor output value in a particular environment 704 based on the areas of the first and second electrodes and/or the spacing therebetween. Each sensor 706 also comprises a sensor material between the first and second electrodes, the electrical behaviour of which is non-linearly (e.g. exponentially) dependent upon the environmental stimulus. When the sensors 706 are capacitive sensors, the sensor material comprises a dielectric material configured to prevent a flow of electrical current between the first and second electrodes in order to produce the respective output value.

The sensor material used will depend on the particular environmental stimulus that is being measured by the sensor array 707. The environmental stimulus may be one or more of the concentration of a chemical or biological species in the environment 704 in which the sensor array 707 is located, the concentration of a liquid or gas in said environment 704, the relative humidity of said environment 704, the temperature of said environment 704, and the pressure applied to one or more sensors 706 of the sensor array 707 (for example). Certain sensor materials (such as graphene oxide) are sensitive to more than one environmental parameter (such as humidity and temperature, as is clear from FIG. 5). With sensing systems comprising such materials, a reference sensor may need to be used in combination with the sensor array so that the effects of any additional environmental parameters can be removed from the raw sensor data. For example, in the case of a graphene oxide-based humidity sensor, a temperature sensor (the reference sensor) may be required in order to evaluate the relative humidity.

The apparatus also comprises a controller (not shown in FIG. 7) configured to control which of the sensors 706 are connected to the common output terminal 708 using respective switches 710 (e.g. analogue switches or field-effect transistors) to vary the effective area and/or spacing of the sensor array 707 such that the array output value at the common output terminal 708, based on the contribution of the respective sensor output values of the connected sensors 706, is held at a reference value. The term "effective area" refers to the combined electrode area of the connected sensors 706, whilst the term "effective spacing" refers to the average electrode spacing of these connected sensors 706.

The present apparatus can be used in two different modes: threshold mode and absolute mode. These will now be described in turn.

Threshold Mode

In threshold mode, the reference value is a substantially constant threshold value, and the controller is configured to control the switches 710 to hold the array output value at the threshold value. In this scenario, a measure of the environmental stimulus can be determined from the configuration of the switches 710. To explain how this works, let's consider that the sensor array 707 (comprising graphene oxide-based sensors 706) is being used to measure the humidity of the surrounding environment 704. Before the sensor array 707 can be used, it needs to be calibrated in a controlled environment (e.g. in an environmentally-controlled chamber).

To begin the calibration, all switches 710 are closed, the humidity is set to zero and the array output value (the threshold value) is recorded. It is important that the threshold value falls within the detectable range (e.g. x→y) of the sensor measurement circuit. In this configuration (which represents the bottom end of the useful input range), every sensor 706 in the array 707 contributes to the array output value. The humidity is then increased gradually causing an increase in the total capacitance of the sensor array 707. To compensate for this increase in capacitance, the controller then opens one of the switches 710 to hold the array output at the threshold value. By opening the switch 710, the effective area of the sensor array 707 is reduced resulting in a decrease in the total capacitance of the sensor array 707. As the humidity increases further, a greater number of switches 710 are opened in order to keep array output value constant (at the threshold value). Whilst this is happening, the switch configuration corresponding to each level of humidity is recorded for later use. Since switches 710 can either be in an open state or a closed state, each of the different switch configurations can be represented by a unique binary number. The process continues until only one switch 710 remains closed. This switch configuration represents the top end of the useful input range.

The sensor array 707 is now able to measure the humidity of the surrounding (external) environment 704. To achieve this, the sensor array 707 is exposed to the environment 704 and the controller cycles through each of the recorded switch configurations in turn until the array output value is equal to the threshold value. Once the threshold value is reached, the corresponding switch configuration is compared with the predetermined calibration data to find a match and the current humidity is determined.

In threshold mode, the accuracy of the sensor array 707 is dependent upon the number of different switch configurations. This is because each configuration corresponds to a specific environmental stimulus value. From an accuracy perspective, therefore, it is better to have a reasonably large number of sensors 706 in the array 707 (although the actual number will vary depending on the desired measurement range).

Absolute Mode

Absolute mode enables an accurate measurement of the environmental stimulus to be made with fewer sensors 806 in the array 807 by taking advantage of the fact that each sensor configuration is capable of being used to measure a range of stimulus values (rather than just a discrete stimulus value) despite the non-linear dependence of the sensor material. In absolute mode, therefore, the reference value is a predefined range, and the controller is configured to control the switches 810 to hold the array output value within the predefined range. In this scenario, a measure of the environmental stimulus can be determined from the configuration of the switches 810 in combination with the absolute array output value for that particular switch configuration.

Figure 8:
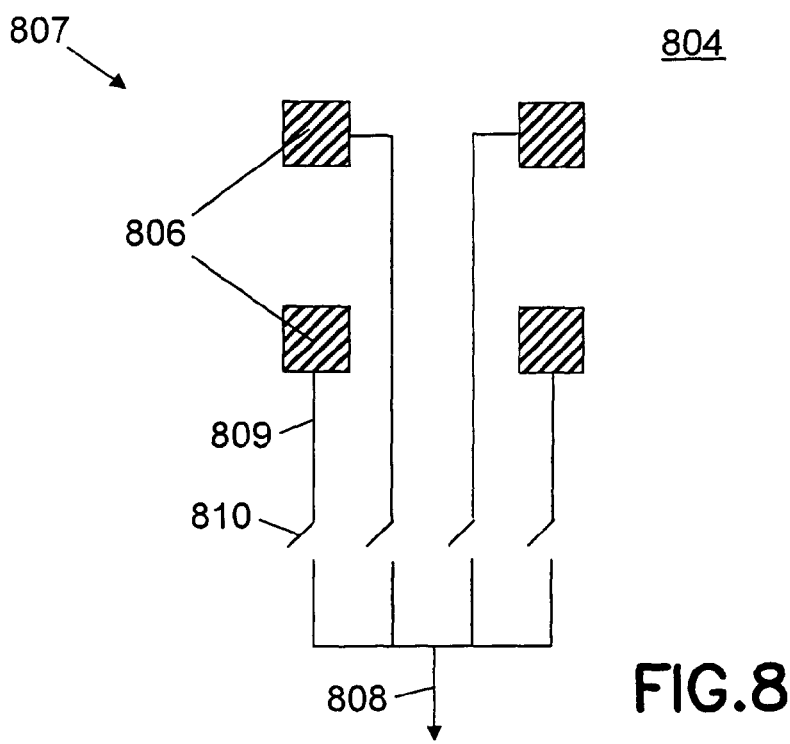
FIG. 8 shows a 2×2 sensor array comprising a plurality of identical sensors connected to a common output terminal by respective switches.

To illustrate this, let's consider that the 2×2 sensor array shown in plan view in FIG. 8 (comprising graphene-based sensors 806) is being used to measure the humidity of the surrounding environment 804. As with threshold mode, the sensor array 807 must be calibrated in a controlled environment (such as the environmentally-controlled chamber) before it can be put to use.

To begin the calibration, all switches 810 are closed to produce a first switch configuration, the humidity is set to zero and the array output value is recorded. It is important that this initial array output value falls within the detectable range of the sensor measurement circuit. The humidity is then increased gradually causing an increase in the total capacitance of the sensor array 807. The output vs humidity data is recorded throughout this process. At some level of humidity (e.g. 25%), the array output value will exceed the detectable range (e.g. x→y) of the measurement circuit resulting in a saturated signal.

Once saturation has been reached, the controller then opens one of the switches 810 to produce a second switch configuration and reduce the effective area of the sensor array 807, and restarts the calibration. The calibration for the second switch configuration may be started from 25% to continue from where the previous calibration left off, or it may be started from a lower humidity (e.g. 0%). As a result of the smaller effective area, the capacitance for a given humidity is reduced relative to the first switch configuration allowing the second switch configuration to be used to measure a different range of humidity. For the purposes of this example, let's assume that the second switch configuration produces an array output value of between x and y when the humidity is between 25% and 50%, beyond which it saturates. The calibration process is then repeated again for the remaining two switch configurations: a third switch configuration comprising two open switches 810; and a fourth switch configuration comprising three open switches 810.

The calibration experiments therefore determine the range of humidity (or other environmental parameter) within which each switch configuration can be used to produce a detectable array output value. In the present case, for example, the calibration experiments might conclude that the first switch configuration can be used to measure humidity values of between 0% and 25%, the second switch configuration can be used to measure humidity values of between 25% and 50%, the third switch configuration can be used to measure humidity values of between 50% and 75%, and the fourth switch configuration can be used to measure humidity values of between 75% and 100%. The calibration experiments also provide output vs humidity (calibration) data for each of the different switch configurations.

Once the calibration is complete, the sensor array 807 can be used to measure the humidity of the surrounding (external) environment 804. To achieve this, the sensor array 807 is exposed to the environment 804, and the controller cycles through each of the recorded switch configurations in turn until the array output value falls within the detectable range of the measurement circuit. Once the array output value falls within the detectable range, the corresponding switch configuration is noted and the absolute output value is compared with the predetermined calibration data for that particular switch configuration to determine the current humidity.

Rather than using an array of identical sensors, the array may comprise a plurality of sensors having different electrode areas and/or spacings. In this way, instead of adjusting the number of sensors connected to the common output terminal in order to hold the array output value at the threshold value (threshold mode) or within the predefined range (absolute mode), the specific sensors which are connected to the common output terminal may be varied. This technique works because, for a given level of humidity (or other environmental parameter), each sensor exhibits a different capacitance and results in a different array output value.

Figure 9:
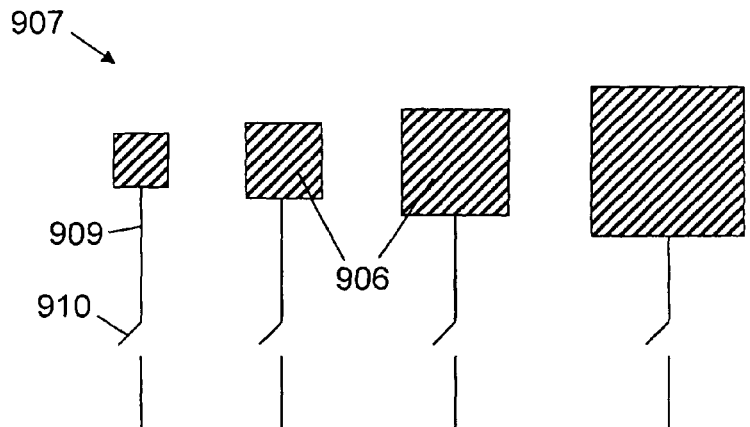
FIG. 9 shows a sensor array in which the electrode area increases from one sensor to the next.

FIG. 9 shows a sensor array 907 (in plan view) comprising four sensors 906, each with a different electrode area. Here, the areas of the first and second electrodes double from one sensor 906 to the next (resulting in a corresponding increase in capacitance for a given humidity), but the area could increase exponentially or by an order of magnitude between adjacent sensors 906 instead. Also, rather than varying the area of both sensor electrodes of the electrode pair, it would be possible to vary the area of one electrode of the pair whilst keeping the other constant. For example, the second electrode could be a layer of electrically conductive material on which the sensor material and first electrode of each sensor 906 are deposited. In this scenario, the second electrode would be common to all sensors 906 in the array 907.

Figure 10:
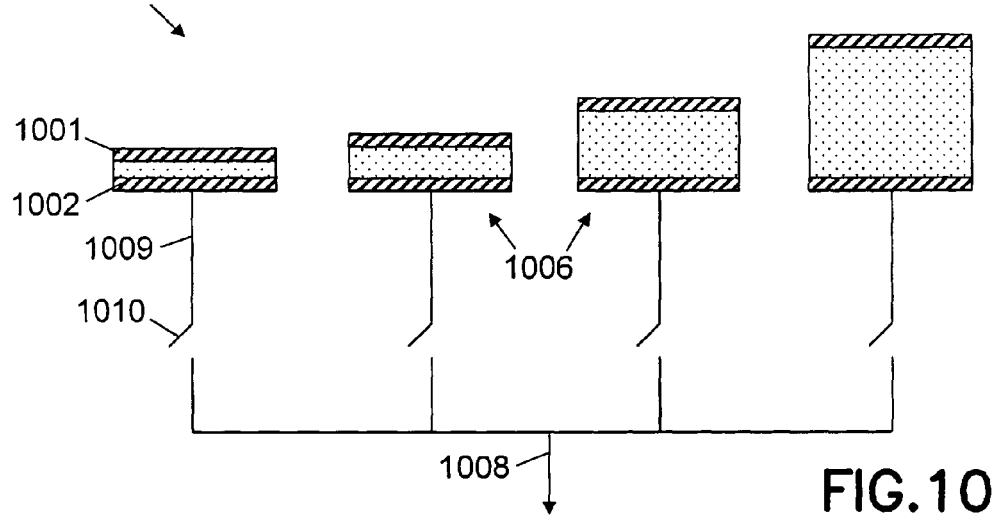
FIG. 10 shows a sensor array in which the electrode spacing increases from one sensor to the next.

FIG. 10 shows another sensor array 1007 (in cross-section) comprising four sensors 1006. This time, instead of varying the areas of the first 1001 and/or second 1002 electrodes, the electrode spacing is varied from one sensor 1006 to the next. As with the electrode area, the spacing between the electrodes 1001, 1002 could double, increase exponentially or increase by an order of magnitude between adjacent sensors 1006.

In practice, it is possible to use both a change in electrode area and a change in electrode spacing in order to hold the array output value at the reference value. For example, each of the sensors 906 shown in FIG. 9 may have a different electrode spacing (as shown in FIG. 10) as well as a different electrode area.

To best compensate for the non-linear sensor behaviour in threshold mode, the sensor array should ideally be configured such that the effective area and/or spacing of the sensor array can be varied according to the same non-linear function. For example, given that the capacitance of graphene oxide varies exponentially with relative humidity, a graphene oxide-based sensor array for measuring relative humidity should be configured such that the effective area and/or spacing of the array varies exponentially from one switch configuration to the next. As a result, the variation in electrode area (FIG. 9) and/or spacing (FIG. 10) between adjacent sensors, or the total number of sensors in the array (FIGS. 7 and 8), will depend on the electrical response of the sensor material to the environmental parameter.

Figure 1B:
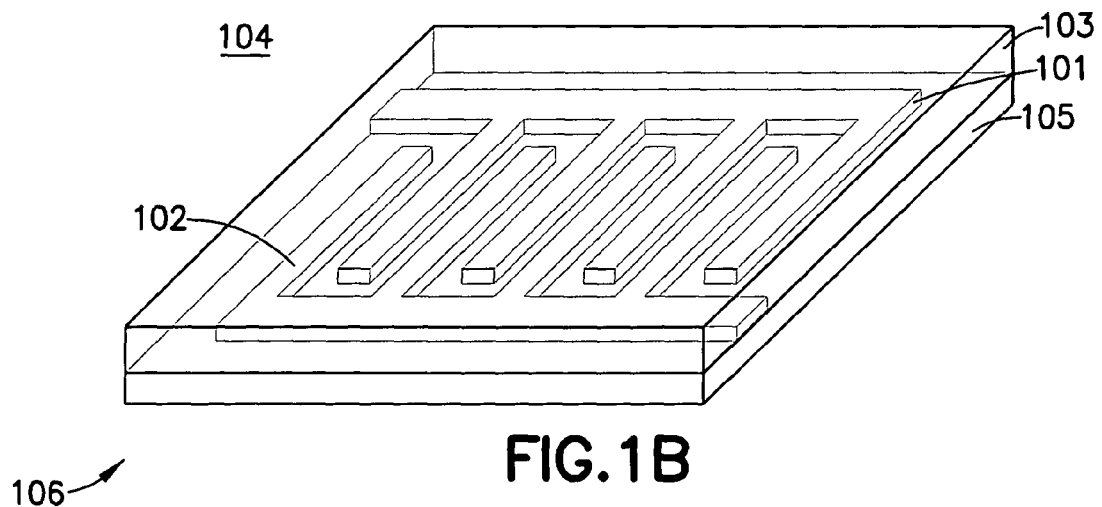
FIG. 1b shows an interdigitated capacitive sensor.

It should be noted that, although the sensor arrays shown in FIGS. 7-10 comprise parallel plate electrodes (as shown in FIGS. 1*a* and 6*a*), the above-mentioned principles can equally be applied using sensors comprising interdigitated electrodes (as shown in FIGS. 1*b* and 6*b*).

Figure 11:
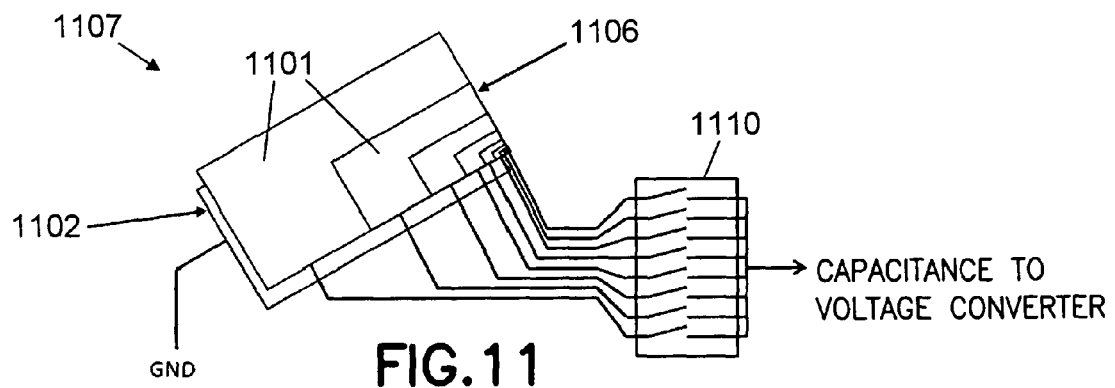
FIG. 11 shows a sensor array having a semi-concentric electrode arrangement.

Furthermore, in the previous examples, the sensors (or their respective first electrodes) have a regular inter-sensor spacing in one, two or possibly three dimensions. For some applications, however, the overall dimensions of the sensor array might be important. This may apply, for example, if the sensor array is to be used in a confined space, in which case device miniaturisation will be a serious consideration. FIGS. 11-13 show some different ways in which the sensors can be arranged to form more compact arrays. In FIG. 11, the first electrodes 1101 of the respective sensors 1106 (although it could be the complete sensors 1106) are arranged to form a semi-concentric array; in FIG. 12, the sensors 1206 (or their respective first electrodes 1201) are arranged to form a fully-concentric array; and in FIG. 13, the sensors 1306 (or their respective first electrodes 1301) are arranged to form a series of adjacent sensors 1306/electrodes 1301 which spiral outward from the centre of the sensor array 1307. In each of these examples, the areas of the first and/or second electrodes increase from one sensor of the array to the next, but the electrode spacing may also vary between adjacent sensors.

Another consideration is whether the sensors in the array are connected to one another in series or in parallel. Although both configurations are possible, the best option will depend (at least partly) on the interface circuit used to convert the array output value into a form which is suitable for use by the controller. For the capacitance-to-voltage converter described with reference to FIGS. 3*a* and 3*b*, the measured voltage is proportional to the capacitance of the sensor. With this type of system, it makes sense to combine the sensors 1406 in parallel (as shown in FIG. 14*a*) so that the effective capacitance of the sensor array 1407 is the sum of the individual sensor capacitances, i.e.

$$C_{\mathit{eff}} = C_1 + C_2 + C_3 + \ldots \qquad \text{Equation 3}$$

For other types of interface circuit, such as a relaxation oscillator, the measurement may be inversely proportional to the capacitance of the sensor. In such a system, it may be more useful to combine the sensors 1406 in series (as shown in FIG. 14*b*) so that the inverse of the capacitance is summed instead, i.e.

$$1/C_{\mathit{eff}} = 1/C_1 + 1/C_2 + 1/C_3 + \ldots \qquad \text{Equation 4}$$

When the sensors 1406 are connected in parallel (as shown in FIG. 14*a*), the common output terminal 1408 is directly connected to the respective outputs of the sensors 1406 via the respective switches 1410. When the sensors 1406 are connected in series (as shown in FIG. 14*b*), however, the common output terminal 1408 is directly connected to the output of the last sensor 1425 in the series and indirectly connected to the respective outputs of the other sensors 1406.

Figure 15:
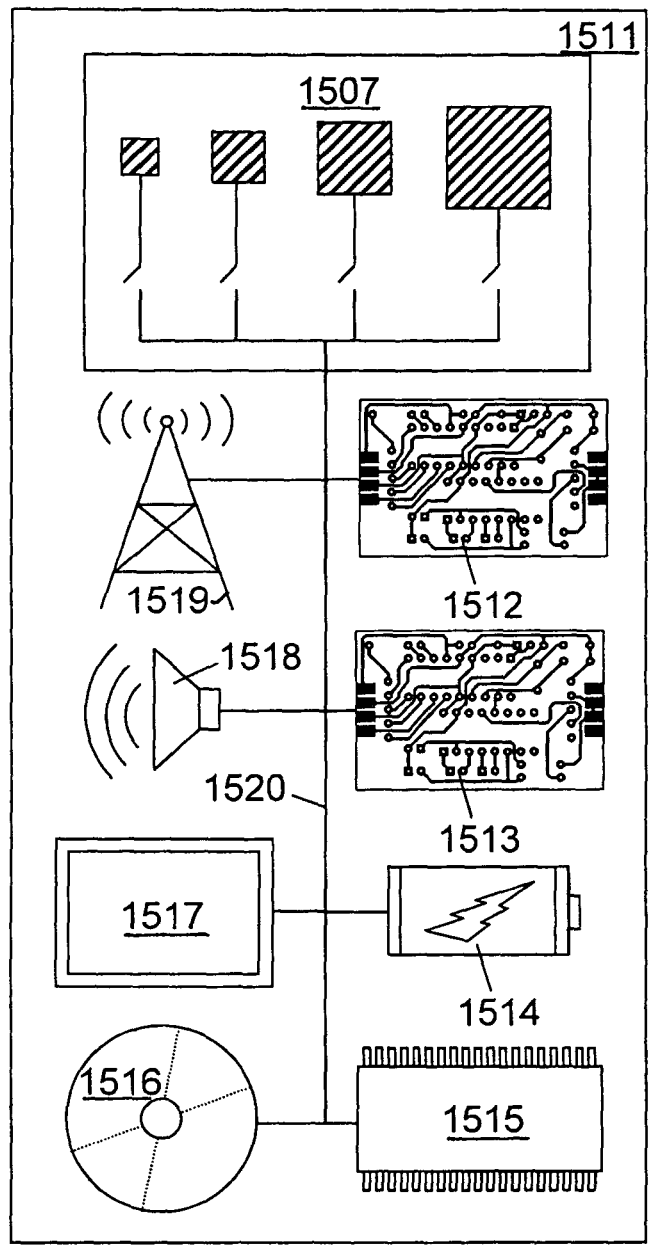
FIG. 15 shows an apparatus comprising the sensor configuration described herein.

FIG. 15 shows one example of the present apparatus. The apparatus may be one or more of an electronic device, a portable electronic device, a portable telecommunications device, a sensor, or a module for one or more of the same. In the example shown, the apparatus is an electronic device 1511 comprising the sensor array 1507 described herein, an interface circuit 1512, a measurement circuit 1513, a battery 1514, a processor/controller 1515, a storage medium 1516, an electronic display 1517, a loudspeaker 1518 and a transmitter 1519, which are electrically connected to one another by a data bus 1520.

As described previously, the sensor array 1507 comprises a plurality of sensors and a common output terminal connected to the respective outputs of the sensors by respective switches. Each sensor comprises first and second electrodes configured to output a respective sensor output value in a particular environment based on the areas of the first and second electrodes and/or the spacing therebetween.

The processor 1515 is configured for general operation of the apparatus 1511 by providing signalling to, and receiving signalling from, the other components to manage their operation. In particular, the processor 1515 is configured to control which of the sensors are connected to the common output terminal using the respective switches to vary the effective area and/or spacing of the sensor array 1507 such that the array output value at the common output terminal, based on the contribution of the respective sensor output values of the connected sensors, is held at a reference value (and therefore acts as a controller). The processor 1515 may also be configured to measure the environmental stimulus based on the switch configuration and calibration data either with (absolute mode) or without (threshold mode) the absolute array output value.

The storage medium 1516 is configured to store computer code configured to perform, control or enable operation of the apparatus 1511. The storage medium 1516 may also be configured to store settings for the other components. The processor 1515 may access the storage medium 1516 to retrieve the component settings in order to manage the operation of the other components. The storage medium 1516 may also be configured to store calibration data (e.g. capacitance vs humidity data) for each of the different switch configurations for use by the processor 1515 in measuring the environmental stimulus.

The processor 1515 may be a microprocessor, including an Application Specific Integrated Circuit (ASIC). The storage medium 1516 may be a temporary storage medium such as a volatile random access memory. On the other hand, the storage medium 1516 may be a permanent storage medium such as a hard disk drive, a flash memory, or a non-volatile random access memory.

The interface circuit 1512 is configured to convert output signals from the sensor array 1507 into a form which is suitable for use by the processor 1515. When the electrical property is capacitance, the interface circuit 1512 may comprise one or more of a capacitance-to-voltage converter, a relaxation oscillator, and a switched capacitor sigma-delta arrangement. The measurement circuit 1513 is configured to measure the array output value, and may comprise an analogue-to-digital converter or a comparator.

The electronic display 1517 is configured to display the measurement of the environmental stimulus to a user of the apparatus 1511; the loudspeaker 1518 is configured to output the measurement as an audio signal (i.e. sound) which is detectable by the user; and the transmitter 1519 is configured to transmit the measurement (and/or the calibration data and array output value) to a remote apparatus such as the user's mobile phone. The transmitter 1519 therefore allows the apparatus 1511 to be positioned at a location which is remote from the user so that the user can monitor the environmental conditions remotely (e.g. via his/her mobile phone).

Figure 16:
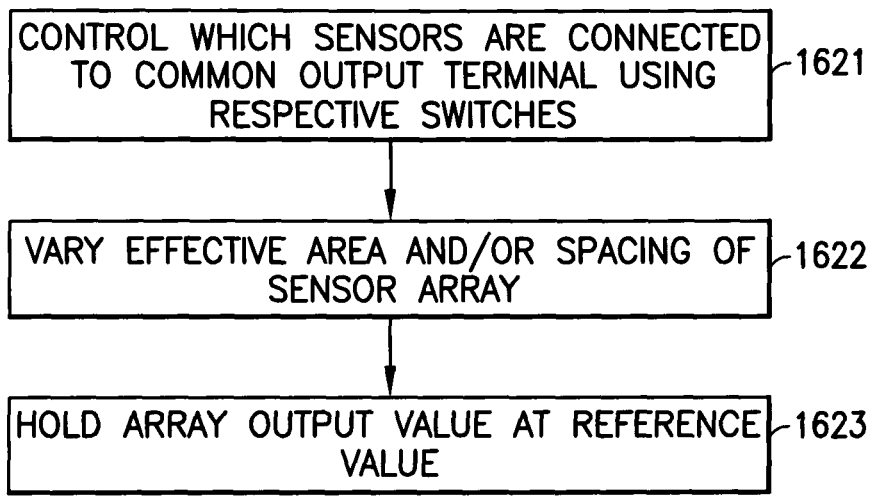
FIG. 16 shows the main steps of a method of using the apparatus described herein.

The main steps 1621-1623 of a method of using the present apparatus are illustrated schematically in FIG. 16.

Figure 17:
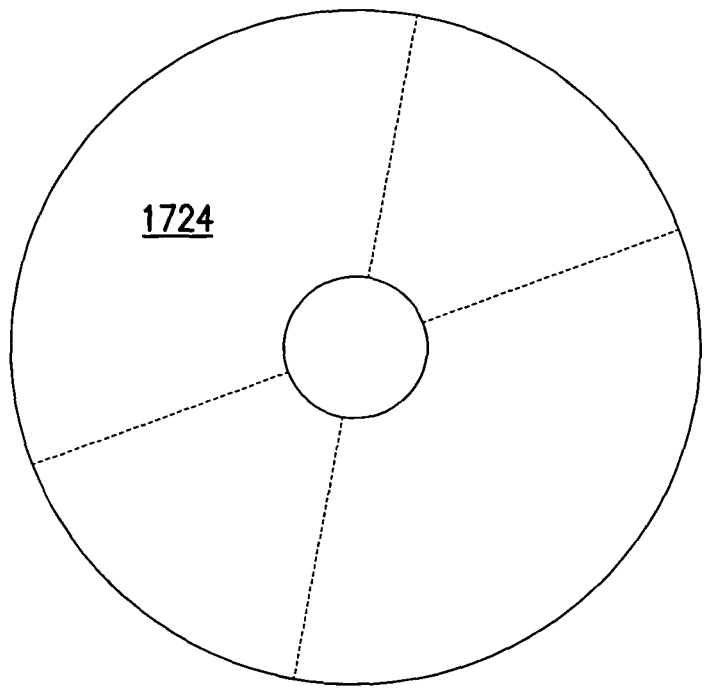
FIG. 17 shows a computer-readable medium comprising a computer program configured to perform, control or enable the method of FIG. 16.

FIG. 17 illustrates schematically a computer/processor readable medium 1724 providing a computer program according to one embodiment. In this example, the computer/processor readable medium 1724 is a disc such as a digital versatile disc (DVD) or a compact disc (CD). In other embodiments, the computer/processor readable medium 1724 may be any medium that has been programmed in such a way as to carry out an inventive function. The computer/processor readable medium 1724 may be a removable memory device such as a memory stick or memory card (SD, mini SD, micro SD or nano SD).

The computer program may comprise computer code configured to perform, control or enable one or more of the method steps 1621-1623 of FIG. 16. In particular, the computer program may be configured to control, with the controller, which of the sensors are connected to the common output terminal using the respective switches to vary the effective area and/or spacing of the sensor array such that the array output value at the common output terminal, based on the contribution of the respective sensor output values of the connected sensors, is held at a reference value.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising a sensor array, configured to produce an array output value in response to an environmental stimulus, and a controller, the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween, the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value or in a reference value.

2. The apparatus of claim 1, wherein the reference value is a substantially constant threshold value and the controller is configured to control the switches to hold the array output value at the threshold value, and wherein the apparatus is configured to enable measurement of the environmental stimulus using the configuration of the switches when the array output value is at the threshold value.

3. The apparatus of claim 2, wherein the apparatus is configured to allow a plurality of different switch configurations, each configuration corresponding to a different environmental stimulus value, and wherein the apparatus is configured to enable measurement of the environmental stimulus using a predetermined calibration of the different switch configurations.

4. The apparatus of claim 1, wherein the reference range is a predefined range and the controller is configured to control the switches to hold the array output value within the predefined range, and wherein the apparatus is configured to enable measurement of the environmental stimulus using the array output value when the array output value is within the predefined range.

5. The apparatus of claim 4, wherein the apparatus is configured to allow a plurality of different switch configurations, each configuration corresponding to a different range of environmental stimulus values, and wherein the apparatus is configured to enable measurement of the environmental stimulus using a predetermined calibration of the current switch configuration in combination with the array output value.

6. The apparatus of claim 1, wherein the apparatus is configured such that the area of the first and/or second electrode of the respective sensors increases between adjacent sensors of the sensor array.

7. The apparatus of claim 6, wherein the area of the first and/or second electrode increases exponentially, doubles or increases by an order of magnitude from one sensor of the sensor array to the adjacent sensor.

8. The apparatus of claim 1, wherein the apparatus is configured such that the spacing between the first and second electrodes of the respective sensors increases between adjacent sensors of the sensor array.

9. The apparatus of claim 8, wherein the spacing between the first and second electrodes increases exponentially, doubles or increases by an order of magnitude from one sensor of the sensor array to the adjacent sensor.

10. The apparatus of claim 1, wherein the sensors, or their respective first electrodes, have a regular spacing in one, two or three dimensions between one another.

11. The apparatus of claim 1, wherein the sensors, or their respective first electrodes, form a concentric or semi-concentric sensor/electrode array.

12. The apparatus of claim 1, wherein the sensors, or their respective first electrodes, are arranged to form a series of adjacent sensors/electrodes which spiral outward from the centre of the sensor array.

13. The apparatus of claim 1, wherein the first and/or second electrodes of the respective sensors are arranged to form an array of interdigitated or parallel plate electrodes.

14. The apparatus of claim 1, wherein the sensors are connected to one another in series or in parallel.

15. The apparatus of claim 1, wherein the sensors are capacitive, resistive or inductive sensors.

16. The apparatus of claim 1, wherein the environmental stimulus is one or more of the concentration of a chemical or biological species in the environment in which the sensor array is located, the concentration of a liquid or gas in said environment, the relative humidity of said environment, the temperature of said environment, and the pressure applied to one or more sensors of the sensor array.

17. The apparatus of claim 1, wherein each sensor exhibits one or more of a non-linear and an exponential response to the environmental stimulus.

18. The apparatus of claim 1, wherein the apparatus is one or more of an electronic device, a portable electronic device, a portable telecommunications device, a sensor, and a module for one or more of the same.

19. A method involving the use of an apparatus,
the apparatus comprising a sensor array, configured to produce an array output value in response to an environmental stimulus, and a controller,
the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween,
the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value,
wherein the method comprises controlling, by the controller, which of the sensors are connected to the common output terminal using the respective switches to vary the effective area and/or spacing of the sensor array such that the array output value at the common output terminal, based on the contribution of the respective sensor output values of the connected sensors, is held at the reference value.

20. A computer program comprising computer code configured to control the use of an apparatus,
the apparatus comprising a sensor array, configured to produce an array output value in response to an environmental stimulus, and a controller,
the sensor array comprising a plurality of sensors and a common output terminal connected to the respective outputs of the sensors, each sensor having first and second electrodes configured to output a respective sensor output value in a particular environment based on the areas of the first and second electrodes and/or the spacing therebetween,
the controller configured to control which of the sensors are connected to the common output terminal using respective switches to vary the effective area and/or spacing of the sensor array such that the array output value at the common output terminal, based on the contribution of the respective sensor output values of the connected sensors, is held at a reference value,
wherein the computer code is configured to control, with the controller, which of the sensors are connected to the common output terminal using the respective switches to vary the effective area and/or spacing of the sensor array such that the array output value at the common output terminal, based on the contribution of the respective sensor output values of the connected sensors, is held at the reference value.

* * * * *

UNITED STATES PATENT AND TRADEMARK OFFICE
CERTIFICATE OF CORRECTION

| | | |
|---|---|---|
| PATENT NO. | : 8,823,396 B2 | Page 1 of 1 |
| APPLICATION NO. | : 13/739452 | |
| DATED | : September 2, 2014 | |
| INVENTOR(S) | : Asttley et al. | |

It is certified that error appears in the above-identified patent and that said Letters Patent is hereby corrected as shown below:

In the Claims

Claim 1, col. 14, line 20 "value" should be deleted and --range-- should be inserted.

Signed and Sealed this
Twenty-fifth Day of November, 2014

Michelle K. Lee
*Deputy Director of the United States Patent and Trademark Office*